US011027273B2

(12) United States Patent
Li et al.

(10) Patent No.: US 11,027,273 B2
(45) Date of Patent: Jun. 8, 2021

(54) APPARATUSES AND METHODS FOR PATHOGEN DETECTION USING MICROFLUIDIC BIOCHIPS

(71) Applicant: THE BOARD OF REGENTS OF THE UNIVERSITY OF TEXAS SYSTEM, Austin, TX (US)

(72) Inventors: Xiujun Li, El Paso, TX (US); Sanjay Timilsina, El Paso, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 643 days.

(21) Appl. No.: 15/555,002

(22) PCT Filed: Mar. 1, 2016

(86) PCT No.: PCT/US2016/020303
§ 371 (c)(1),
(2) Date: Aug. 31, 2017

(87) PCT Pub. No.: WO2016/140990
PCT Pub. Date: Sep. 9, 2016

(65) Prior Publication Data
US 2018/0036727 A1    Feb. 8, 2018

Related U.S. Application Data

(60) Provisional application No. 62/126,659, filed on Mar. 1, 2015.

(51) Int. Cl.
*B01L 3/00* (2006.01)
*G01N 33/543* (2006.01)
*G01N 33/558* (2006.01)

(52) U.S. Cl.
CPC ...... *B01L 3/5027* (2013.01); *G01N 33/54366* (2013.01); *G01N 33/54373* (2013.01); *G01N 33/558* (2013.01); *B01L 2300/069* (2013.01); *B01L 2300/0816* (2013.01); *B01L 2300/0819* (2013.01); *B01L 2300/0829* (2013.01); *B01L 2300/0864* (2013.01); *B01L 2300/0887* (2013.01); *B01L 2300/123* (2013.01); *B01L 2300/126* (2013.01)

(58) Field of Classification Search
USPC .................................................... 435/287.9
See application file for complete search history.

(56) References Cited

U.S. PATENT DOCUMENTS

| | | | |
|---|---|---|---|
| 6,083,682 A * | 7/2000 | Campbell | B01J 19/0046 422/130 |
| 6,485,690 B1 * | 11/2002 | Pfost | B01J 19/0046 422/552 |
| 6,827,095 B2 | 12/2004 | O'Connor | 137/15.01 |
| 2001/0001644 A1 * | 5/2001 | Coffman | B01L 3/50255 422/534 |
| 2001/0003648 A1 * | 6/2001 | Pantoliano | G01N 33/6845 435/4 |
| 2002/0185431 A1 * | 12/2002 | Karp | B01L 3/502753 210/488 |
| 2003/0202909 A1 * | 10/2003 | Atkinson | B01L 3/50255 422/400 |
| 2004/0149659 A1 * | 8/2004 | Kane | B01L 3/50255 210/649 |
| 2005/0072030 A1 * | 4/2005 | Wu | G09F 3/02 40/324 |
| 2005/0142033 A1 * | 6/2005 | Glezer | B01L 3/5085 422/400 |
| 2006/0205061 A1 * | 9/2006 | Roukes | G01N 33/54366 435/287.2 |
| 2008/0113357 A1 * | 5/2008 | Baggio | C12N 15/1017 435/6.19 |
| 2009/0123336 A1 | 5/2009 | Yang | 422/68.1 |
| 2011/0236264 A1 | 9/2011 | Rajogopal | 422/82.07 |
| 2012/0328488 A1 | 12/2012 | Puntambekar et al. | 422/503 |
| 2012/0329163 A1 * | 12/2012 | Faber | B01L 3/50255 436/86 |
| 2013/0052653 A1 | 2/2013 | Stein | 435/7.1 |
| 2013/0143254 A1 * | 6/2013 | Thomas | G01N 33/54373 435/29 |
| 2015/0011437 A1 * | 1/2015 | Zhang | B01L 3/5085 506/39 |
| 2016/0201037 A1 * | 7/2016 | Tuan | C12M 23/12 435/373 |
| 2017/0029809 A1 * | 2/2017 | Suh | C12N 15/1003 |

OTHER PUBLICATIONS

International Preliminary Report on Patentability in International Application No. PCT/US2016/020303 dated Sep. 14, 2017.
International Search Report and Written Opinion in International Application No. PCT/US2016/020303 dated Jul. 15, 2016.

* cited by examiner

*Primary Examiner* — Ann Y Lam
(74) *Attorney, Agent, or Firm* — Norton Rose Fulbright US LLP

(57) ABSTRACT

Certain embodiments are directed to a paper hybrid microfluidic microplate. In certain aspects, the hybrid microfluidic microplate is a low-cost, sensitive, and fast diagnostic apparatus for detecting pathogens, diagnosing disease and other bio-applications, especially for low-resource settings.

2 Claims, 12 Drawing Sheets

APPARATUSES AND METHODS FOR PATHOGEN DETECTION USING MICROFLUIDIC BIOCHIPS

CROSS-REFERENCE TO RELATED APPLICATION

This Application is a national phase application under 35 U.S.C. § 371 of International Application No. PCT/US2016/020303, filed Mar. 1, 2016, which claims the benefit of priority of the filing date of U.S. Provisional Patent Application 62/126,659 filed on Mar. 1, 2015, by the inventors of this application. Both applications are hereby incorporated by reference in their entirety.

TECHNICAL FIELD OF THE INVENTION

The present disclosure relates generally to microfluidic biochip apparatuses and related methods. More particularly, the disclosure relates to hybrid microfluidic microplate apparatuses comprising three or more layers. These apparatuses are incorporated into methods for pathogen detection in a sample.

BACKGROUND

Acute infectious diseases caused by various pathogenic microorganisms like viruses, bacteria, fungi, and parasites have been the major cause of global death and disability throughout human history. Cancer is another disease that figures among the leading cause of death worldwide with 8.2 million deaths in 2012 (Kovarik et al., (2011) *Analytical chemistry* 84, 516-540). Diagnosis and protection against these diseases has been hampered by the inability to recognize the disease, pathogen or virus species, strains, virulence factors, and antimicrobial susceptibilities in a timely manner. These diseases are usually diagnosed by pathology or exhausting immunoassay tests such as ELISA (Enzyme Linked Immune Sorbent Assay), immunofluorescence, western blotting, and immunodiffusion. Although, science and technology are progressing, an automatically operating immunosensor for the rapid and sensitive simultaneous detection of multiple diseases or biological agents in the field is still a challenge.

Infectious diseases, cancer, and other diseases are often diagnosed by immunoassay. ELISA, one of the most commonly and widely used laboratory immunoassay methods in medical diagnostic and research applications, detects proteins based on their binding to immobilized antibodies or antigens. Even though most ELISAs today are performed in 96-well plates and are well-suited for high-throughput assays, the assay methods are highly complicated and specialized instruments have to be utilized to automate the assay, including robotic pipetters, plate washers, and spectrophotometers. These traditional quantitative immunoassay experiments take several hours to complete because of the hour-long incubation. Likewise, another critical issue is the consumption of large volumes of precious samples and reagents, and the requirement of performing the assays in a laboratory setting, which is often not suitable for point-of-care detection of pathogenic diseases.

A review of commercially available microfluidic immunoassays or protein diagnostic chip microarrays is provided in Chin et al., (2012) (*Lab on a Chip,* 2012, 12, 2118-2134). Microfluidics immune assay uses various techniques for sample analysis, which include, colorimetric, electrochemical, electrochemiluminescence, thermal lens microscopy, electrochemical detection in combination with nanoparticles, super-paramagnetic beads, microcantilever transducer combined with an impedance analyzer, absorbance and fluorescence methods. Similarly, microfluidics focusing on multiple sample analysis relies on parallel microchannel immunoassay, microfluidic bead arrays, arrayed electrodes, affinity microcolumns, electrokinetically controlled immunoassay and compact disc immunoassay. Many of these microfluidics-based detection methods are complex and require large and expensive equipment, which limit their application in developing countries and in point of care settings which require high throughput pathogen detection. It remains a challenge to fabricate a portable microfluidic immunoassay apparatus, with a detection method that is visible to the naked eye, for use in detection pathogens in the field. Thus, there is a need for rapid, efficient, and sensitive apparatuses and methods for point of care detection of pathogens.

SUMMARY

In view of the aforementioned problems and trends, general embodiments of the present disclosure provide apparatuses and methods for pathogen detection using microfluidic biochips.

Certain embodiments are directed to microfluidic biochips that are paper-polymer hybrid systems. In certain aspects the biochips are low-cost, sensitive, and fast diagnostic apparatuses for detecting pathogens and diagnosing disease.

Certain embodiments are directed to a microplate as disclosed herein for immunoassays.

In certain aspects, apparatuses and methods described herein are used for detection of one or more pathogens. In certain aspects the apparatuses detect one or more bacterial, fungal, viral, or parasite pathogens. The apparatus can be configured to be a point of care apparatus that can be used in remote and crude environments. In a further aspect, the apparatuses and methods can be used, for example, to detect bacteria, such as those bacteria that cause meningitis, pertussis, and other infections. The apparatuses and methods can be used to detect a plurality of pathogens.

In certain aspects, the apparatus detects one or more biomarkers of cancer and/or other diseases.

Certain embodiments are directed to polymer/paper based hybrid microfluidic apparatuses of three or more layers.

Any suitable material or materials may be used to form the microfluidic apparatus or components thereof (e.g., the top, middle, and/or bottom layers).

In certain embodiments, the microfluidic apparatus is partially a paper apparatus, i.e. a hybrid apparatus.

In certain aspects, the microfluidic apparatus can comprise one or more microwells or chambers.

Certain embodiments are directed to methods of detecting a target or pathogen, which includes the steps of introducing a sample suspected of having or comprising a target or pathogen into an apparatus described herein and subjecting the sample to antibody detection, wherein if a target is present in the sample an antibody binds to a target and can be detected.

In certain aspects, the apparatus is configured to detect a plurality of targets at once (multiplexed assay) with a separate and distinct antibody/antigen in an individual detection microwell. In certain aspects, a single detection microwell can have two or more antibodies/antigens that can be distinguish from each other. In certain aspects the target is a pathogen or a cancer biomarker, such as a food borne pathogen. The pathogen can be a bacterium, a fungus, a parasite, a virus, or combinations thereof.

Other aspects of the embodiments described herein will become apparent from the following description and the accompanying drawings, illustrating the principles of the embodiments by way of example only.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

FIG. 1 is a composite illustration of the chip design of the present disclosure, wherein FIGS. 2A-2E depicts various views of the chip design of the PMMA/Paper based hybrid microfluidic apparatus of the present disclosure wherein FIG. 2A is a top perspective view of top layer, I; FIG. 2B is a top perspective view of middle layer, II; FIG. 2C is another top perspective view of middle layer, II; FIG. 2D is a top perspective view of bottom layer, III, and FIG. 2E is a cross-section view of the chip, FIG. 6A illustrates fluorescence intensity of Cy-3 IgG from left to right (100 µg/mL, PBS, 50 µg/mL, PBS, 25 µg/mL, PBS, 12.5 µg/mL, and PBS) after 10 minutes of incubation and three times of washing with PBST while FIG. 6B illustrates the average mean intensity of fluorescence of 20 µg/mL of Cy-3 IgG with and without blocking buffer, FIGS. 8A-8B depict various aspects of a calibration curve for the detection of IgG on a chip wherein FIG. 8A is a sigmoidal curve of IgG over a concentration range of $1 \times 10^2$ µg/mL to $1 \times 10^8$ µg/mL; FIG. 8B is an enzymatic converted substrate in different columns of the chip with varying concentrations of IgG, FIGS. 9A-9B depict various aspects of a calibration curve for the detection of HBsAg on a chip wherein FIG. 9A is a sigmoidal curve of HBsAg over a concentration range of $3.4 \times 10^2$ µg/mL to $3.4 \times 10^8$ µg/mL and FIG. 9B is an enzymatic converted substrate in different columns of the chip with varying concentrations of HBsAg, FIGS. 10A-10B illustrate the detection of HBcAg on a paper/PMMA hybrid microfluidic microplate, wherein FIG. 10A is an enzymatic converted substrate in different columns of the chip with varying concentrations of HBcAg and FIG. 10B is a sigmoidal curve of HBcAg over a concentration range of 1 ng/mL to $1 \times 10^5$ ng/mL, FIGS. 11A-11B illustrate a multiplex assay on a paper/PMMA hybrid microfluidic microplate, wherein FIG. 11A depicts a scanned image of the enzyme-catalyzed substrate, while FIG. 11B is a bar plot of corrected brightness of the scanned image for detection of HBsAg and HBcAg, and FIGS. 12A-12B depict the results of an anti-interference test for the detection of HBsAg on a paper/PMMA hybrid microfluidic microplate, wherein FIG. 12A is a bar graph of the corrected brightness of the scanned image of ELISA as measured by ImageJ of the scanned image of the chip in FIG. 12B.

NOTATION AND NOMENCLATURE

Figure 1A:
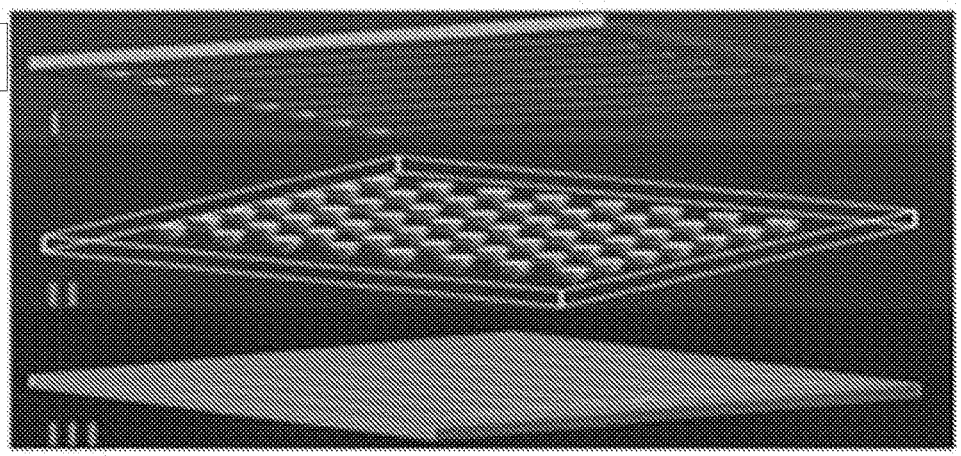
FIG. 1A depicts a 3D schematic diagram of three different layers, top layer (I), middle layer (II), and bottom layer (III)

Certain terms are used throughout the following description and claims to refer to particular system components and configurations. As one skilled in the art will appreciate, the same component may be referred to by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device or apparatus couples to a second device or apparatus, that connection may be through a direct connection, or through an indirect connection via other devices or apparatuses and connections.

The term "probe" refers to a molecule that can detectably distinguish between target molecules differing in structure. Detection can be accomplished based on identification of specific binding with a target. Examples of such specific binding include antibodies, antibody fragments, or other affinity reagents.

The term "antibody" as used herein includes immunoglobulin molecules and immunologically active portions of immunoglobulin molecules, i.e., molecules that contain an antigen-binding site that specifically binds (immunoreacts with) an antigen. The term "antibody" as used herein also includes antibody-like molecules, such as aptamers. A naturally occurring antibody (e.g., IgG, IgM, IgD) includes four polypeptide chains, two heavy (H) chains and two light (L) chains interconnected by disulfide bonds. However, it has been shown that, fragments of a naturally occurring antibody can perform the antigen-binding function of an antibody. Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989); and (vi) a F(ab')$_2$ fragment Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Falkner et al., Nature 298:286, 1982; Morrison, J. Immunol. 123:793, 1979; Morrison et al., Ann Rev. Immunol 2:239, 1984).

The phrase "specifically binds" to a target refers to a binding reaction that is determinative of the presence of the target in the presence of a heterogeneous population of other biologics. Thus, under designated conditions, a specified molecule binds preferentially to a particular target and does not bind in a significant amount to other biologics present in the sample.

As used herein, the term "sample" or "test sample" generally refers to a material suspected of containing one or more targets. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, lysing microbes in the sample, and the like. Methods of treatment may involve filtration, precipitation, dilution, distillation, mixing, concentration, inactivation of interfering components, lysing organisms and/or cells, and the addition of reagents. Besides physiological fluids, other liquid samples may be used such as water, food products, and the like for the performance of environmental or food production assays. In addition, a solid material suspected of containing the target may be used as the test sample. In some instances it may be beneficial to modify a solid test sample to form a liquid medium or to release a target (e.g., a nucleic acid).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the apparatus or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "providing" is used according to its ordinary meaning to indicate "to supply or furnish for use."

Protein Composition(s): As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed in generating an immune response. The terms "protein" and "polypeptide" may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function. It is specifically contemplated that a modified/variant protein or polypeptide may be altered with respect to one activity or function yet retain a wild-type activity or function in other respects, such as immunogenicity.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

As used herein, an "amino molecule" refers to any amino acid, amino acid derivative, or amino acid mimic known in the art. In certain embodiments, the residues of the proteinaceous molecule are an amino molecule which is sequential, without any non-amino molecule interrupting the sequence of amino molecule residues. In other embodiments, the sequence of the proteinaceous molecule may comprise one or more non-amino molecule moieties. In particular embodiments, the sequence of residues of the proteinaceous molecule may include one or more amino molecules interrupted by one or more non-amino molecule moieties/molecules.

Accordingly, the term "proteinaceous composition" encompasses amino molecule sequences comprising at least one of the 20 common amino acids in naturally synthesized proteins, or at least one modified or unusual amino acid.

The term "functionally equivalent codon" is used herein to refer to codons that encode the same amino acid, such as the six codons for arginine or serine, and also refers to codons that encode biologically equivalent amino acids: Alanine (A) GCA, GCC, GCG, GCU; Cysteine (C) UGC, UGU; Aspartic acid (D) GAC, GAU; Glutamic acid (E) GAA, GAG; Phenylalanine (F) UUC, UUU; Glycine (G)

GGA, GGC, GGG, GGU; Histidine (H) CAC, CAU; Isoleucine (I) AUA, AUC, AUU; Lysine (K) AAA, AAG; Leucine (L) UUA, UUG, CUA, CUC, CUG, CUU; Methionine (M) AUG; Asparagine (N) AAC, AAU; Proline (P) CCA, CCC, CCG, CCU; Glutamine (Q) CAA, CAG; Arginine (R) AGA, AGG, CGA, CGC, CGG, CGU; Serine (S) AGC, AGU, UCA, UCC, UCG, UCU; Threonine (T) ACA, ACC, ACG, ACU; Valine (V) GUA, GUC, GUG, GUU; Tryptophan (W) UGG; and Tyrosine (Y) UAC, UAU.

Nucleic Acid(s): As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. It also is contemplated that a particular polypeptide may be encoded by nucleic acids containing variations having slightly different nucleic acid sequences but, nonetheless, encode the same or substantially similar protein.

As used herein the phrase "immune response" or its equivalent "immunological response" refers to the development of a humoral (antibody mediated), cellular (mediated by antigen-specific T cells or their secretion products) or both humoral and cellular response directed against a protein in a recipient patient. Such a response can be an active response induced by administration of immunogen or a passive response induced by administration of antibody, antibody containing material, or primed T-cells.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present invention encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

Microfluidic immunoassay apparatuses provide high surface-to-volume ratio and microliter volume of microchannels that leads to significant decreases in analysis time from hours to minutes with minimal reagent utilization as compared to regular ELISA technology. Generally the present disclosure teaches a simple miniature (56/64) well sample ELISA in microfluidics chip to eliminate the need for manual fluid handling and the use of sophisticated instruments. The present disclosure teaches a point of care, economical and easy to detect, low volume portable microfluidic chip for highly sensitive and specific disease detection, which does not require manual pipetting of the reagents into the wells. The use of paper as the apparatus substrate, as it is inexpensive, easy to obtain and fabricate, is disclosed herein. This paper-based substrate provides a substrate for simple antigen immobilization, without any chemical modification of the surface. Also, the paper provides the 3D surface for the immobilization of the antigen or the antibody. As such, a paper-based ELISA is much faster, with results in an hour.

The microfluidic apparatuses described herein can be used in remote regions such as those found in underdeveloped and developing countries, in emergency situations, or in home health-care settings for early, easy and fast medical diagnosis. Steven Sun et al. reported ELISA-LOC (Sun et. al., (2010), Lab on chip, 10, 2093-2100) with a washing step integrated into the system but the system is complex, consisting of seven plates. Additionally, it requires manual addition of CNT-primary antibody and SEB and also, the apparatus has to be reassembled during the assay procedure, before integrating the washing step.

Protein immobilization on one of the most commonly used platform PDMS (Polydimethylsiloxane) relies on physical adsorption, which may result in strong non-specific binding. Protein covalent immobilization can be improved by plasma oxidation or ultraviolet irradiation to improve PDMS hydrophilicity, ultimately reducing the non-specific binding, while enhancing biological activity and stability. However, these methods are based on high-energy sources and are very difficult to carry out in an assembled microfluidic apparatus due to its deeply embedded microchannels in the PDMS slab.

PMMA, poly (methyl methacrylate) has various advantages over other expensive substrates. It is more rigid and less fragile, disposable and easy to fabricate using techniques such as hot embossing or $CO_2$ laser ablation. Also, it does not require the longer fabrication and incubation time that is required for PDMS.

Various substrates including PDMS, PMMA, PC, and paper have been used for the fabrication of microfluidic apparatuses. Each substrate has its own advantages and disadvantages. Polymers such as PMMA, PDMS, and PC are transparent and easy to fabricate. PMMA is compatible with most substrate unlike polydimethylsiloxane (PDMS). In addition, PMMA is more rigid and less fragile, disposable and does not require longer fabrication and incubation time as required by other substrates like PDMS. Polymers such as PMMA and PDMS require complicated surface modification procedures to immobilize biosensors and other biomolecules such as antibodies and enzymes.

ELISA has been reported in PMMA apparatus but they require complicated surface modification including poly (ethyleneimine) (PEI) treatment, (3-aminopropyl)triethoxy silane (APTES) treatment, and carbon nanotube (CNT) functionalization. In addition, they require detectors like fluorescence microscopy. Paper-based apparatuses can rapidly immobilize biosensors and other biomolecules but do not offer high performance in flow control. Hybrid apparatuses can be used to take advantages of various substrates and eliminates some disadvantages of the substrates. Recently, hybrid apparatuses have been used for various applications.

Portable, two and three-dimensional microfluidic analytical devices are described for performing multiplexed assays. The disclosed hybrid microfluidic microplate devices require the addition of one or more drops of sample and one or a more drops of water to perform the multiplexed assays. In preferred embodiments, all the reagents, buffer salts, analytes (e.g., antigens), and binders (e.g., antibodies) used for the assays may be stored within the device. The results of the multiple assays can be quantitative or qualitative.

The present disclosure also teaches the development of PDMS/paper/glass hybrid microfluidic biochips for one-step multiplexed pathogen detection taking advantages of all the substrates. Glass provides the support; PDMS controls the flow of liquid while paper acts as the substrate for the immobilization of aptamer-functionalized nano-biosensors.

With the emergence of paper-based apparatuses in recent years, various point of care (POC) analyses, including paper based ELISA, low cost colorimetric diagnostic assays and HIV chips, have been developed. Results have been demonstrated by expensive and cumbersome means such as video camera or digital color analyzer, or scanner. Of course, the simplest and easiest means of detection relies on viewing by the naked eye. The paper based ELISA with detection based on viewing by the naked eye, as disclosed herein, takes advantage of the sensitivity and specificity of an ELISA and low cost, easy to use and detect paper.

Paper-based apparatuses do not require a clean room for fabrication, can transport liquid via capillary effect, and do not require external force. Another significant feature of paper is the high surface to volume ratio of the micro-porous structure, which improves the immobilization of protein and other biological agents. Paper-based ELISA takes advantage of sensitivity and specificity of an ELISA and low cost, easy-to-use paper. Others have performed ELISA in a 96-microzone plate fabricated in paper. Although it was faster and less expensive than conventional ELISA, it was almost 10-fold less sensitive than conventional ELISA. Other limitations in paper-based ELISA include bad flow control and the need for repeated micro pipetting for adding reagents and washing in 96 wells, which limits its application for high-throughput detection.

Microfluidic immunoassay apparatuses possess remarkable features such as high surface-to-volume ratios and microliter volume of microchannel that leads to significant decrease in analysis time from hours to minutes and with minimal reagent utilization as compared to regular ELISA technology. This is highly desirable for diagnosis and treatment of disease in people in remote regions such as those found in underdeveloped and developing countries, in emergency situations, or in home health-care settings where there is a need for early, easy and fast medical diagnosis.

Hepatitis B virus (HBV) infection is a major cause of chronic hepatic damage and of hepatocellular carcinomas worldwide. HBsAg, a qualitative serological biomarker for a developing HBV infection, can diagnose acute and chronic hepatitis B virus. Also, the titer of serum HBsAg indicates the level of infection and severity of disease. IgG can serve as a specific marker for Neuromyelitis optica, an inflammatory demyelinating disease.

The present disclosure teaches a simple miniaturized (56) well paper/PMMA hybrid microfluidic ELISA microplate for rapid and high-throughput detection of infectious diseases. A novel funnel shaped PMMA has been created by laser ablation of PMMA, wherein a paper substrate can be placed to perform the ELISA within an hour. The novel use of 3D micro-porous paper with high surface-to-volume ratios inserted in microwells of this hybrid microplate, facilitates rapid immobilization of antibody/antigen and avoids complicated surface modifications. The top reagent delivery channel along with the vertical flow-through wells in the middle PMMA layer can simply transfer reagents to multiple wells. These vertical flow-through wells avoid repeated manual pipetting and washing steps into each well, in conventional ELISA or the use of costly robots.

Both the reagent delivery and washing steps are integrated into the apparatus. All the reagent/analyte passes through the 3D matrix of the paper surface from the funnel shaped well before reaching the outlet channel, giving the large 3D surface area for the immobilization of antibody/antigen, ultimately increasing the sensitivity of the ELISA. ELISA of IgG and HBsAg were performed in the hybrid apparatus and LODs comparable to commercial ELISA kits were obtained.

Disclosed herein is the fabrication of a POC, economical and easy to detect, portable microfluidic chip for highly sensitive and specific disease detection. The hybrid microfluidic microplate is small, less expensive, and does not require trained personnel and considerable volumes of biological samples and can be used for various bioassays.

Any suitable material or materials may be used to form the microfluidic apparatus or components thereof (e.g., the top, middle, and/or bottom layers). For example, the apparatus or components thereof may be fabricated from inorganic materials including glass, silica, silicon, metal, plastics or polymers, including dendritic polymers, such as poly(vinyl chloride), poly(vinyl alcohol), poly(methyl methacrylate), poly(vinyl acetate-maleic anhydride), poly(dimethylsiloxane)monomethacrylate, cyclic olefin polymers and copolymers including copolymers of norbornene and ethylene, fluorocarbon polymers, polystyrenes, polypropylene, polyethyleneimine; copolymers such as poly(vinyl acetate-co-maleic anhydride), poly(styrene-co-maleic anhydride), polysaccharide, polysaccharide peptide, poly(ethylene-co-acrylic acid) or derivatives of these or the like. The materials for forming the apparatuses or components or parts thereof may be selected based on desired mechanical or other properties for optimizing target detection. In certain aspects the apparatus is made of a polymer, such as but not limited to polysiloxane (e.g., polydimethysiloxane (PDMS)); polymethyl-methacrylate (PMMA), polycarbonate (PC), or cyclic olefin copolymer (COC). In further aspects the middle layer is a siloxane polymer, such as, but not limited to polydimethysiloxane (PDMS). In certain aspects the bottom layer is glass, PMMA, PDMS, PC, or COC. In certain aspects the polymer is polymethyl-methacrylate (PMMA).

In certain embodiments the microfluidic apparatus is partially a paper apparatus, i.e. a hybrid apparatus. Paper is a thin material produced by pressing together moist fibers, typically cellulose pulp derived from wood or grasses and drying them into flexible sheets. In certain aspects paper is cellulose, nitrocellulose, nylon, or other material that forms a sheet or a membrane. The thickness of paper is often measured by caliper, which is typically given in thousandths of an inch. Paper is often characterized by weight. In the United States, the weight assigned to a paper is the weight of a ream (500 sheets) before the paper is cut to size. For example, a ream of 20 lb, 8.5 in×11 in (216 mm×279 mm) paper weighs 5 pounds, because it has been cut from a larger sheet into four pieces. The density of paper ranges from 250 kg/m$^3$ (16 lb/cu ft) for tissue paper to 1,500 kg/m$^3$ (94 lb/cu ft) for some specialty paper. In certain aspect the paper is a porous blotting paper having a thickness of 0.5 to 2 mm, including all values there between. In a further aspect the paper is chromatography paper having a thickness 0.05 to 0.25 mm and pores having a diameter of 5 to 15 μm. The paper can be designed to be hydrophilic and interact with liquids and solutions in certain locations and treated in other areas so as to be hydrophobic. A paper microapparatus can be designed to have hydrophobic regions that form channels and chambers that allow the flow of solutions within the microapparatus. For example, the paper can be treated to be hydrophobic, e.g., treated with wax or other chemical that is integrated in the paper or coats the paper rendering it hydrophobic. Paper can be cut into appropriate shapes and/or layered so as to produce a microfluidic apparatus when combined with a polymer to form a hybrid apparatus.

In certain aspects a microfluidic apparatus can comprise one or more microwells or chambers. In certain aspects a micro well can comprise two portions, an upper well portion and a lower well portion. A microwell without different diameters can have different depths (e.g. 1, 2, 3, or 4 mm in depth, including all values there between). In certain aspects the well can taper from 2 to 4 mm in diameter at the top of the well to 0.2 to 1.0 mm at the bottom of the well. In certain aspects the apparatus can be loaded without using complicated surface modification procedures for probe immobilization. A probe mixture can be preloaded into microwells. In certain aspects a probe is coupled to a detectable label, e.g., a fluorescent label.

Samples

The apparatuses described herein can be used for assaying small volumes of biological samples, e.g., fluid samples. Biological samples that can be assayed using the devices described herein include, e.g., urine, whole blood, blood plasma, blood serum, sputum, cerebrospinal fluid, ascites, tears, sweat, saliva, excrement, gingival cervicular fluid, or tissue extract. In some embodiments, the volume of fluid sample to be assayed may be a drop of blood, e.g., from a finger prick, or a small sample of urine, e.g., from a newborn or a small animal. In other embodiments, the devices described herein can be used for assaying aqueous fluid samples such as industrial fluid or a water sample. The devices may also be adapted for assaying non-aqueous fluid samples for detecting, e.g., environmental contamination.

Under many aspects, a single drop of liquid, e.g., a drop of blood from a pinpricked finger, is sufficient to perform assays providing a simple yes/no answer to determine the presence of an analyte, or a semi-quantitative measurement of the amount of analyte that is present in the sample, e.g., by performing a visual or digital comparison of the intensity of the assay to a calibrated color chart. However, to obtain a quantitative measurement of an analyte in the liquid, a defined volume of fluid is typically deposited in the device. Thus, in some embodiments, a defined volume of fluid (or a volume that is sufficiently close to the defined volume to provide a reasonably accurate readout) can be obtained by patterning the paper to include a sample well that accepts a defined volume of fluid. For example, in the case of a whole blood sample, the subject's finger could be pinpricked, and then pressed against the sample well until the well was full, thus providing a satisfactory approximation of the defined volume.

Analytes

The assay reagents included in the disclosed devices are selected to provide a visible indication of the presence of one or more analytes. The source or nature of the analytes that may be detected using the disclosed devices are not intended to be limiting. Exemplary analytes include, but are not limited to, toxins, organic compounds, proteins, peptides, microorganisms, bacteria, viruses, amino acids, nucleic acids, carbohydrates, hormones, steroids, vitamins, drugs, pollutants, pesticides, and metabolites of or, antibodies to, any of the above substances. Analytes may also include any antigenic substances, haptens, antibodies, macromolecules, and combinations thereof. For example, immunoassays using the disclosed devices could be adopted for antigens having known antibodies that specifically bind the antigen.

In exemplary embodiments, the disclosed devices may be used to detect the presence or absence of one or more viral antigens, bacterial antigens, fungal antigens, or parasite antigens, cancer antigens. Exemplary viral antigens may include those derived from, for example, the hepatitis A, B, C, or E virus, human immunodeficiency virus (HIV), herpes simplex virus, Ebola virus, varicella zoster virus (virus leading to chicken pox and shingles), avian influenza virus, SARS virus, Epstein Barr virus, rhinoviruses, and coxsackieviruses. Exemplary bacterial antigens may include those derived from, for example, *Staphylococcus aureus, Staphylococcus epidermis, Helicobacter pylori, Streptococcus bovis, Streptococcus pyogenes, Streptococcus pneumoniae, Listeria monocytogenes, Mycobacterium tuberculosis, Mycobacterium leprae, Corynebacterium diphtherias, Borrelia burgdorferi, Bacillus anthracia, Bacillus cereus, Clostridium botulinum, Clostridium difficile, Salmonella typhi, Vibrio chloerae, Haemophilus influenzae, Bordetella pertussis, Yersinia pestis, Neisseria gonorrhoeae, Treponema pallidum, Mycoplasm sp., Legionella pneumophila, Rickettsia typhi, Chlamydia trachomatis, Shigella dysenteriae,* and *Vibrio cholera.* Exemplary fungal antigens may include those derived from, for example, *Tinea pedis, Tinea corporus, Tinea cruris, Tinea unguium, Cladosporium carionii, Coccidioides immitis, Candida sp., Aspergillus fumigatus,* and *Pneumocystis carinii.* Exemplary parasite antigens include those derived from, for example, *Giardia lamblia, Leishmania sp., Trypanosoma sp., Trichomonas sp.,* and *Plasmodium sp.* Exemplary cancer antigens may include, for example, antigens expressed, for example, in colon cancer, stomach cancer, pancreatic cancer, lung cancer, ovarian cancer, prostate cancer, breast cancer, liver cancer, brain cancer, skin cancer (e.g., melanoma), leukemia, lymphoma, or myeloma.

In other embodiments, the assay reagents may react with one or more metabolic compounds. Exemplary metabolic compounds include, for example, proteins, nucleic acids, polysaccharides, lipids, fatty acids, amino acids, nucleotides, nucleosides, monosaccharides and disaccharides. For example, the assay reagent is selected to react to the presence of at least one of glucose, protein, fat, vascular endothelial growth factor, insulin-like growth factor 1, antibodies, and cytokines.

Certain embodiments are directed to a low-cost point of care (POC) apparatus for rapid and high-sensitivity pathogen detection in resource-poor settings. Certain aspects provide a low cost approach for microbe detection through the use of paper-based microfluidics, e.g., all-paper or partially paper microfluidic apparatuses. Because of the miniaturization of reactions carried out in microfluidic systems, low reagent consumption is an intrinsic advantage that reduces costs associated with reagents and materials. In addition, paper is inexpensive and easy to obtain.

MICROFLUIDIC APPARATUS DESIGN AND FABRICATION

Figure 1B:
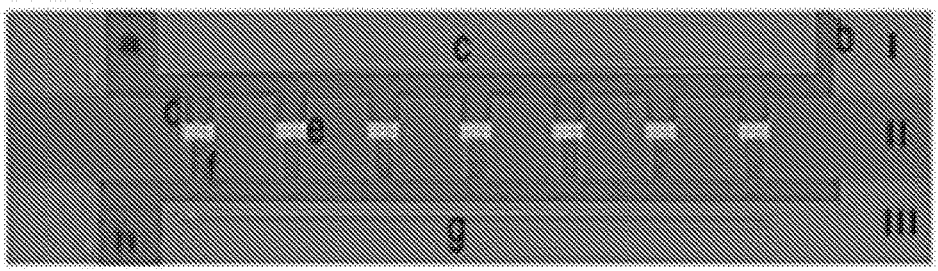
FIG. 1B depicts the direction of the flow of a reagent via a cross section view of the chip.
Figure 1C:
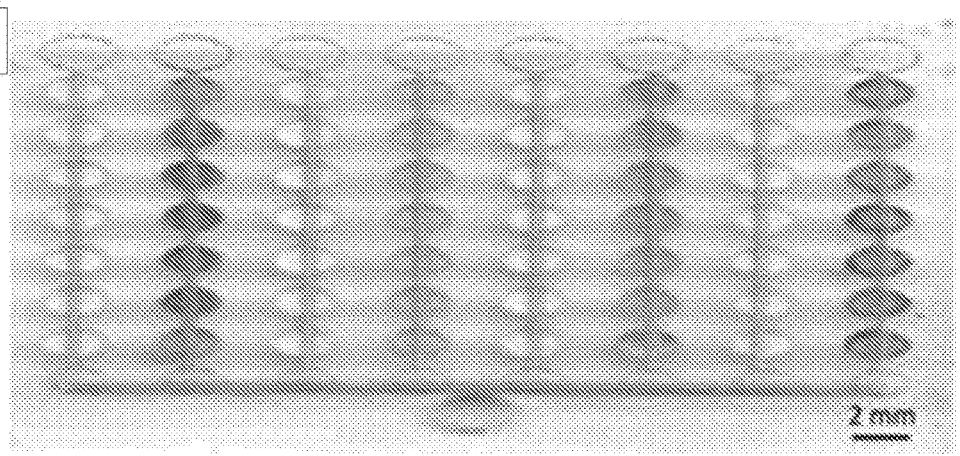
FIG. 1C depicts the fully assembled microfluidic chip with different food dyes.

FIG. 1 is a composite illustration of the chip design of the PMMA/paper hybrid microfluidic microplate of the present disclosure. FIG. 1A is a 3D schematic diagram of three different layers, top layer (I), middle layer (II), and bottom layer (III). FIG. 1B is a cross-section view of the chip. The chip consists of three PMMA layers. The top layer (I), for fluid delivery consist of inlet hole a, and fluid distribution channel c. The middle layer (II), incubation and detection well consist of a unique funnel shaped well, with upper well d of diameter 2 mm and lower well f of 0.3 mm, with a 2 mm paper e placed in between. The lowermost layer (III), fluid removal layer consist of an outlet channel g, which leads to a common outlet hole h. FIG. 1C illustrates an apparatus of the present disclosure with different colored dyes in alternate columns, with Milli-Q water in an adjacent column with no color.

As depicted in FIG. 1A, the topmost 1.5 mm PMMA layer consists of 8-inlet hole connected to 8 channels (200 µm wide and 200 µm deep). As reagent/analyte is added to the inlet hole, it flows through the channels in the upper layer. The middle layer (2 mm PMMA) consists of 7×8 (56) array of funnel shaped well, which is placed just below the 8 channels so that the reagent from the channel falls directly into the wells. The bottom layer (1.5 mm PMMA) consists of outlet channels (200 µm wide and 200 µm deep). Each channel is located just below the lower hole of the well so all the excess reagent falls down to the channel which flows towards the common outlet. The direction of the flow of the reagent can be seen from the cross section view of the chip (FIG. 1B).

For binding of the PMMA apparatus, different PMMA layers were clamped together and kept in an oven at 115-120° C. for 35 minutes. The chip could be used once it cooled down to room temperature. FIG. 1C shows the photograph of the fully assembled microfluidic chip with different food dyes. Different PMMA layers could be separated after the test by applying pressure between the joints so that the apparatus can be reused after cleaning.

Figure 2A:
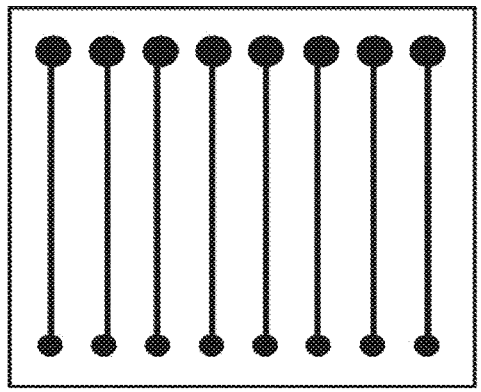
Figure 2B:
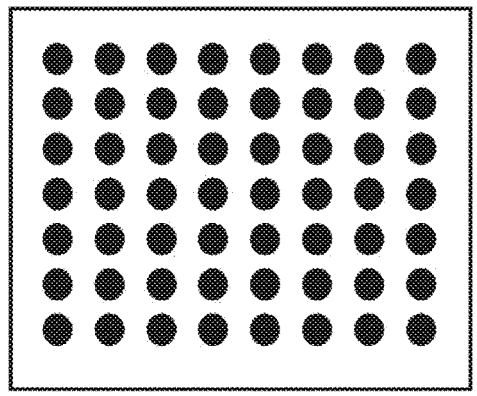
Figure 2C:
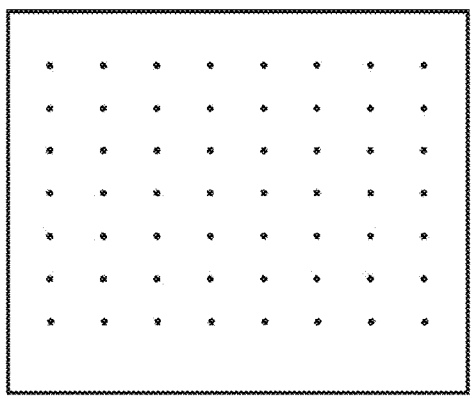
Figure 2D:
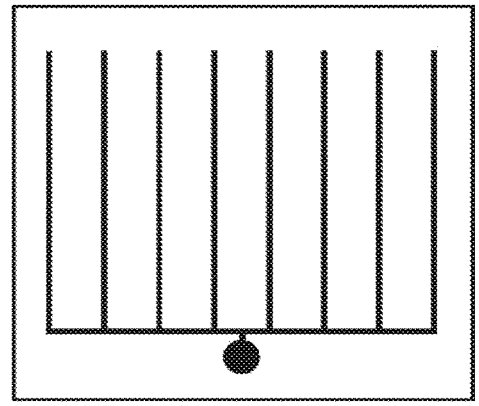
Figure 2E:
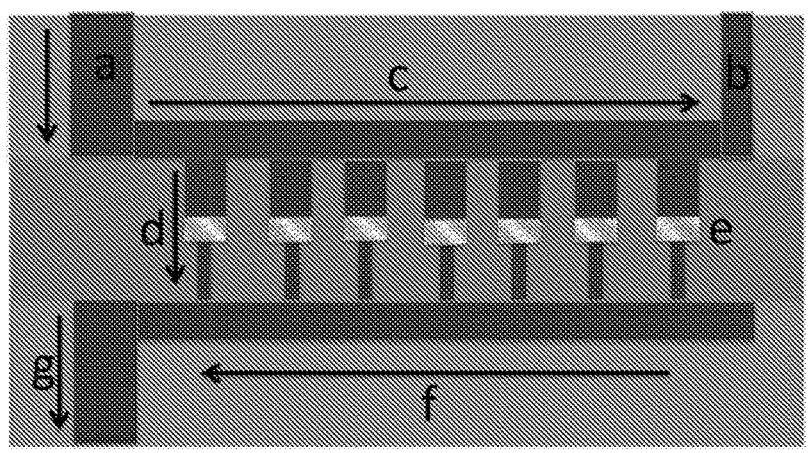

In certain embodiments, a chip was designed in Adobe Illustrator CS5 and micro-machined using Laser cutter (Epilog Zing 16, Golden, Colo.). As shown in FIGS. 2A-2E, the microfluidic apparatus consists of three different layers, all of which were PMMA. Illustrated are schematic diagrams of these three different layers, top layer (I), middle layer (II), and bottom layer (III). FIG. 2A is a top view of the top layer. FIG. 2B is a top view of the middle layer (upper portion of the wells). FIG. 2C is a top view of the middle layer (lower portion of the wells). FIG. 2D is a top view of the bottom layer. FIG. 2E is a cross-section view of the chip.

An exemplary chip consists of three PMMA layers. The top layer (I), for fluid delivery consists of inlet hole a, pressure vent b, and fluid distribution channel c. The middle layer (II), incubation and detection well consist of a unique funnel shaped well d, with upper well of diameter 2 mm and lower well of 0.3 mm, with a 2 mm paper e placed in between. The lowermost layer (III), fluid removal layer, consists of an outlet channel f, which leads to a common outlet hole g.

A polymer/paper apparatus may have three layers, a top layer (I), a middle layer (II) and a bottom layer (III). The top layer (I), for fluid delivery comprises one or more inlets and fluid distribution channels. The middle layer (II), incubation and detection well comprises one or more detection wells. In certain aspects the detection well is a funnel shaped well, with different upper well diameters (e.g. about 1, 2, 3, 4, or 5 mm, including all values and ranges there between), and lower well diameters (e.g. 0.1, 0.2, 0.3, 0.4, 0.5, to 1 mm, including all values and ranges there between). Lower well diameters are smaller than upper well diameters. In certain aspects a paper insert is positioned between the upper well and the lower well or positioned at the bottom of the upper well where it is supported partially by the rim of the lower well. The lowermost layer (III), fluid removal layer consist of at least an outlet channel, which leads to a common outlet hole or multiple outlet holes. In certain aspects, the apparatus may have more than 3 layers.

Certain embodiments are directed to microfluidic biochips that are low-cost, sensitive, and fast diagnostic apparatuses for detecting infectious diseases. In certain aspects apparatuses and methods described herein are used for detection of pathogenic cells, bacterial, fungal, viral, or parasite pathogens in remote and crude environments. In a further aspect, the apparatuses and methods can be used, for example, to detect bacteria, such as those bacteria that cause meningitis, pertussis, and other infections. The apparatuses and methods can be used to detect a number of pathogens.

The topmost layer, the fluidic delivery system also forms the cover for the wells in the assay plate (middle layer) and is used to deliver all the assay reagents. Each of the channels, connected to different inlet hole of upper layer, delivers reagents to middle layer (2 mm diameter), 7 wells placed just below the channel, so that reagents from inlet channel falls directly to the wells in the second layer. Pieces of chromatography paper (diameter 2.0 mm) was cut using a laser cutter and placed inside each well, as a 3D surface for the ELISA. Chromatography paper can also be placed just over the middle layer, so that the paper pieces directly fall to each well in the middle layer once laser cutter cuts it. Middle layer is a funnel shaped PMMA with upper diameter of 2 mm and lower diameter of 0.3 mm, wherein a paper substrate can be placed. 0.3 mm diameter, lower well that is placed just below the upper well of middle layer helps to hold the paper in place and minimizes the chances of backflow of the reagents. Just below the bottom of the assay well, is attached the outlet system. The outlet channels are positioned under the holes on the bottom of the wells all of which are connected to a single outlet well, which acts as an outlet hole once a negative pressure is applied.

As seen in the example provided in FIG. 2A, the topmost 1.5 mm PMMA layer consists of 8-inlet hole connected to 8 channels (200 µm wide and 200 µm deep). When reagent is added to the inlet hole it flows through the channels in lower portion of the upper layer. The middle layer (2 mm PMMA) consists of 56 (8×7) array of funnel shaped well, which is placed just below the 8 channels so that the reagent from the channel falls directly into the wells. Although only 56 wells are used in this apparatus as a demonstration of the proof of concept, this could be scaled up to 384 wells or more. The bottom layer (1.5 mm PMMA) consists of outlet channels (200 µm wide and 200 µm deep). Each channel is located just below the lower hole of the well so all the excess reagent falls down to the channel which flows towards the common outlet. The direction of the flow of the reagent can be seen from the cross section view of the chip (FIG. 2E).

For binding of the PMMA apparatus, different PMMA layers were clamped together and kept in oven at 115-120° C. for 35 minutes and let it cool down to room temperature. Strong bonding was observed. Colored dye was used to test if there was any unanticipated leakage or mixing between different channels. Different colored dye was added to every alternate column in the chip. Also, for the leakage or cross contamination test, Cy-3 labeled IgG was added to the alternate column of the chip and in the adjacent columns PBS was added. Different PMMA layers could be separated after the test by applying pressure between the joints so that the apparatus can be reused after cleaning.

Figure 3:
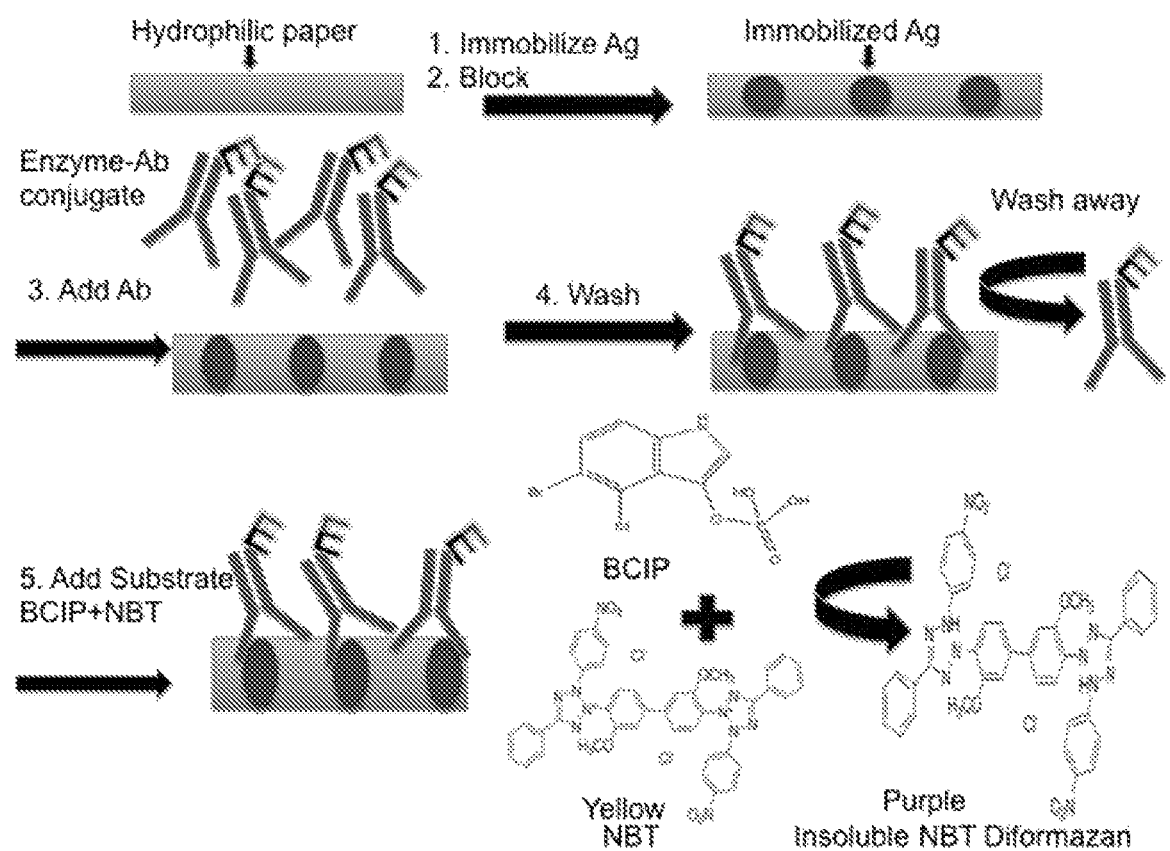
FIG. 3 illustrates the schematic approach of the enzymatic immunoassay of the present disclosure on paper which comprises five steps.

FIG. 3 is a schematic illustration of the approach of enzymatic immunoassay on paper comprising five steps: (1) immobilizing antigens on paper, (2) blocking, (3) antibody/antigen binding, (4) washing, and (5) Enzymatic production of Insoluble NBT Diformazan.

Figure 4:
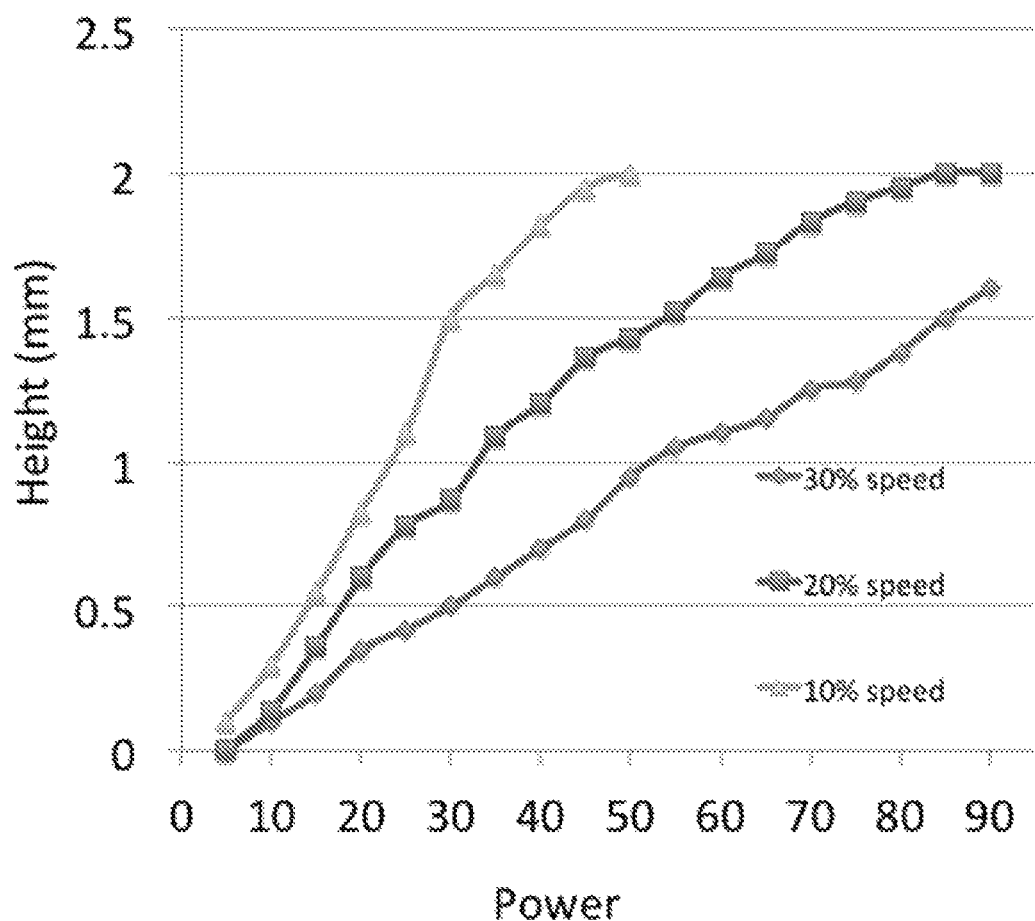
FIG. 4 depicts laser ablation of PMMA at different speed and power, and the corresponding depth obtained in the PMMA.

FIG. 4 depicts laser ablation of PMMA at different speed and power, and the corresponding depth obtained in the PMMA. The graph shows the depth of the well achieved by speed of 10%, 20% and 30% respectively at different power.

Two-Level Laser Fabrication of PMMA. Laser cutter was used to cut different channels and wells of various heights, including funnel shaped well in the middle layer. The chip used for this example was designed in Adobe Illustrator CS5 and micro-machined using Laser cutter (Epilog Zing 16, Golden, Colo.). The Laser power and speed for cutting polymers was determined empirically. The raster mode was used for cutting PMMA layer while vector method was used for cutting Chromatography paper.

The laser power and speed required for cutting the paper and PMMA was empirically determined. Speed of 50 and power of 5% (30 W laser) was optimum for cutting the chromatographic paper in the vector mode. For cutting of PMMA raster mode was used. A chart was prepared by using different speed and power to cut the PMMA layer. The chart was then used to find the required speed and power optimal for ablating wells and channels of different height. As seen from FIG. 3, it can be observed that the speed of 10 and power of 50% could completely pass through the 2 mm PMMA creating a hole. Similarly for 1.5 mm PMMA speed of 10 and power of 30% was used. Likewise to create an upper well (2 mm diameter and 0.7 mm height) speed of 30 and power of 40% was used. Similarly, to create a lower well (0.3 mm in diameter and 1.3 mm height), speed of 30 and power of 75% was used. To create a lower well just below the upper well, the design was first created in adobe illustrator CS5, so as to make it exactly below the upper well and two different print command was given respectively, without moving the chip from its place.

Hybrid Microfluidic Apparatus. Once all the three different PMMA layers were laser ablated and chromatography papers were kept in the wells, the three layers were kept in their respective position one above the other, they were clamped and kept in the oven at 115° C. for 35 minutes. After the chip was cooled down to room temperature, fluorescein isothiocyanate was added to the alternate column of the chip and in the adjacent columns Milli Q water was added.

Figure 5:
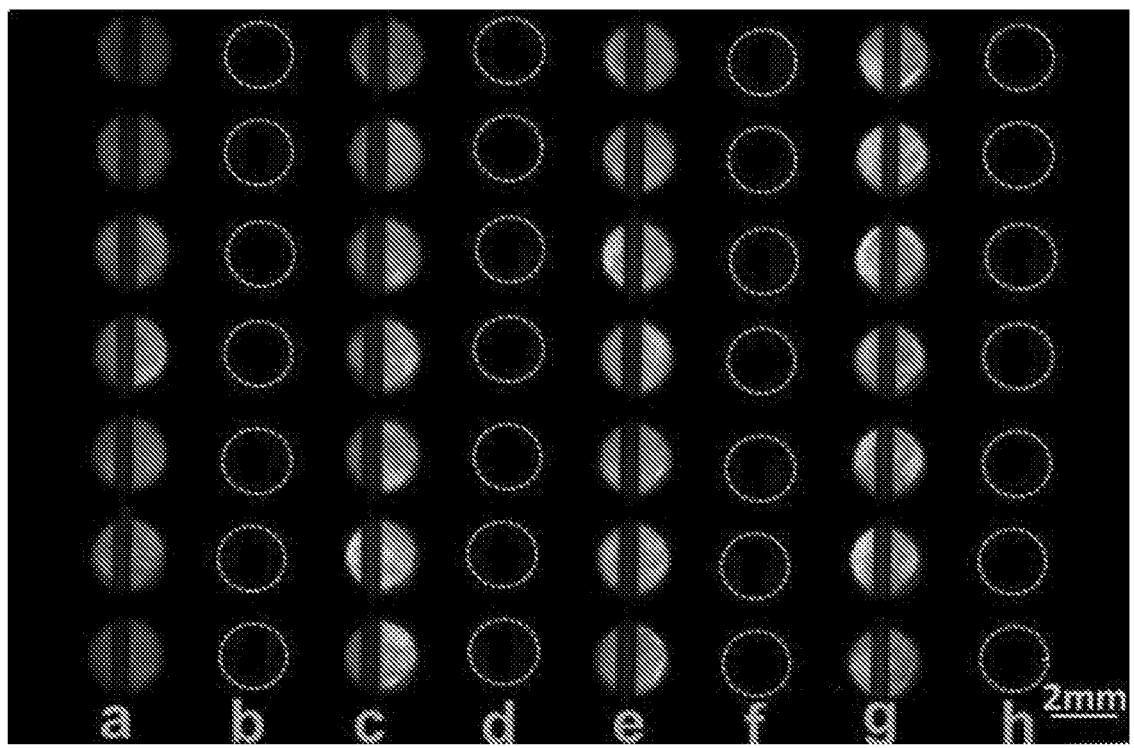
FIG. 5 illustrates the results of a cross contamination/Leakage test.

FIG. 5 illustrates a cross contamination/Leakage test. FITC was added to column a, c, e, and g where fluorescence can be seen and in the adjacent columns b, d, f and h, Milli-Q water was added where no fluorescence was observed. As illustrated in FIG. 5, there is high fluorescent intensity only in the alternate column (a, c, e, g) where FITC was added and there is no fluorescence in adjacent column (b, d, f, h). The result shows that there is no cross contamination or leakage within the different columns Different colors of dyes were similarly passed into the alternate column, with water in the adjacent column to do the leakage test and get rid of the microscope. Similar results were obtained with colors showing up only in the alternate column and white background in the adjacent column.

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Immobilization and Detection of IgG

Figure 6A:
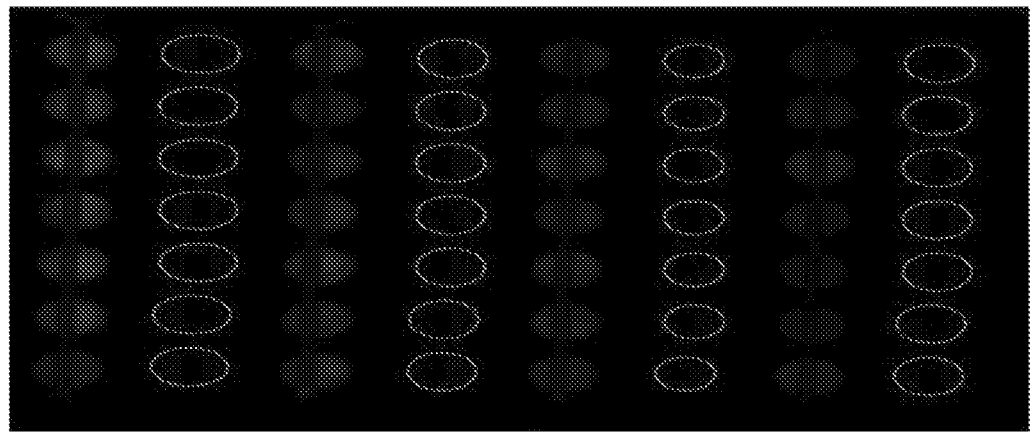
FIGS. 6A-6B depict the effectiveness of adsorption of antibody, washing, and blocking buffer. Specifically.

Cy-3 labeled IgG was used to assess the immobilization of antibody on a paper surface. Different concentration of Cy-3 labeled IgG (100, 50, 25, and 12.5 µg/mL) was added to every alternate channel, with PBS in the adjacent channel and allowed to immobilize on the paper surface for 10 minutes. Antibody immobilized zones in the paper apparatus were imaged before and after washing three times with PBST to see the effectiveness of binding and washing. FIG. 6 illustrates the effectiveness of adsorption of antibody, washing, and blocking buffer. FIG. 6A teaches the decreasing fluorescence intensity of Cy-3 IgG from left to right (100 µg/mL, PBS, 50 µg/mL, PBS, 25 µg/mL, PBS, 12.5 µg/mL, and PBS) after 10 minutes of incubation and three times of washing with PBST. Decreasing intensity of fluorescence with the decrease in concentration of Cy-3 IgG can be seen in the alternate columns and there was no fluorescence in the columns where only PBS was added as depicted in FIG. 6A.

Figure 6B:
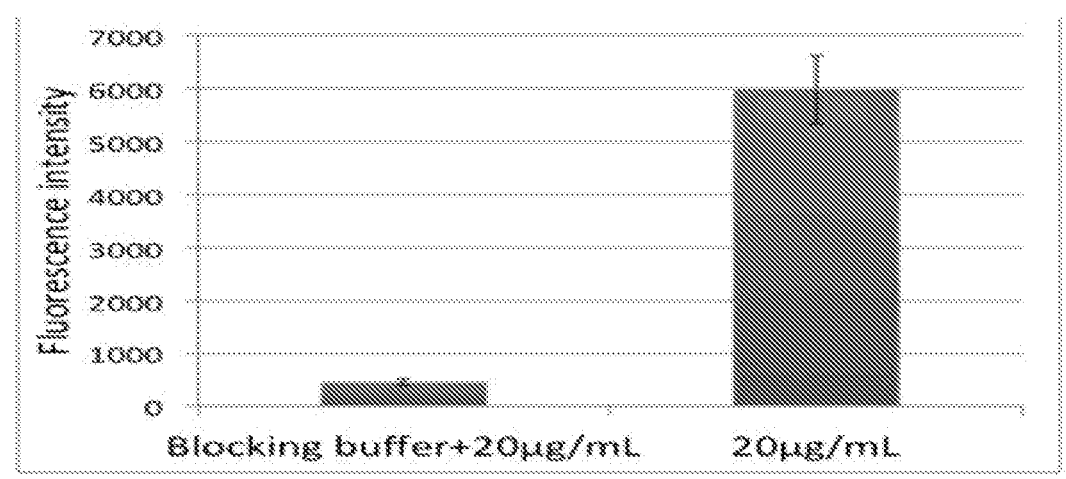

FIG. 6B illustrates the average mean intensity of fluorescence of 20 µg/mL of Cy-3 IgG with and without blocking buffer. Also, in order to determine the effectiveness of blocking buffer, 4% BSA+0.05% Tween 20 was added to one column of the chip and incubated for 10 minutes after which Cy-3 IgG was added. In the other column only Cy-3 IgG was added to check the effectiveness of blocking buffer. Both the columns were washed with washing buffer (PBST) for three times, after which the fluorescence intensity was measured. FIG. 6B shows that the blocking buffer effectively blocks the paper since minimal fluorescence can be seen in the columns where Cy-3 IgG was added after the blocking buffer.

It was observed that once BCIP/NBT was added to the chip, the substrate system starts producing an insoluble diformazan end product that is purple in color and can be observed visually. The color intensity significantly increases with time and it starts fading away after a while. To know the optimum time for the incubation and scanning, ELISA of IgG (1 ng/mL-1 µg/mL) was done in chip, and the chip was scanned every 5 minutes, after 10 minutes of addition of BCIP/NBT.

Figure 7:
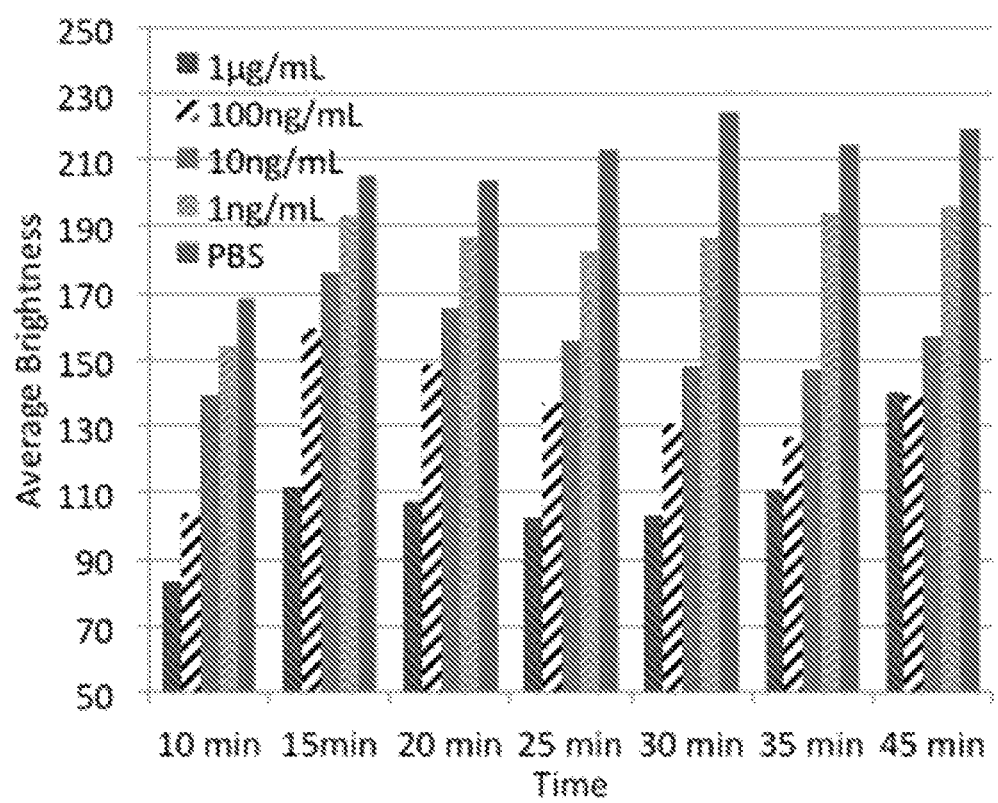
FIG. 7 is a graph illustrating the average brightness value as measured by ImageJ for different IgG concentration (PBS, 1 ng/mL, 10 ng/mL, 100 ng/mL and 1 µg/mL) at different times (10-45 minutes) after addition of the substrate BCIP (5-bromo-4chloro-3-indoyl-phosphate)/NBT (nitro blue tetrazolium)

FIG. 7 is a graph shows the average brightness value as measured by ImageJ for different IgG concentration (PBS, 1 ng/mL, 10 ng/mL, 100 ng/mL and 1 µg/mL) at different time (10-45 minutes) after addition of the substrate BCIP (5-bromo-4chloro-3-indoyl-phosphate)/NBT (nitro blue tetrazolium). As seen from FIG. 7, color develops up to 25 minutes, after which the color starts fading away. Also, higher signal/noise ratio (the noise is derived from the column with PBS which don't contain IgG) can be seen at 25 minutes. Thus, 25 minutes incubation time was considered optimum and the chip was scanned after 25 minutes in subsequent experiments.

For IgG detection assay, the primary Antibody, IgG (0.1 ng/mL-100 µg/mL in 10 mM, pH 8.0 PBS) was introduced in the chip from different inlet holes in the first layer of the chip. After the chip was incubated with primary antibody for 10 minutes, the unreacted paper surface was blocked with Bovine Serum Albumin (4% BSA w/v in PBS+0.05% Tween 20) for another 10 minutes. After that, it was washed with washing buffer, PBST (10 mM, pH 7.4 PBS+0.05% Tween 20). Following washing, anti-rabbit IgG-Alkaline phosphatase (29 µg/mL) was added. It was then incubated for another 7 minutes, followed with washing by the washing buffer for three times. Finally, the substrate for the alkaline phosphatase, i.e., BCIP/NBT (Nitroblue tetrazolium+5-bromo, 4-chloro, 3-indoyl phosphate) was added. NBT is used with the alkaline phosphatase substrate BCIP in western blotting and immunohistological staining and immunoassay procedures. These substrate systems produce an insoluble NBT diformazan, end product that is blue to purple in color and can be observed visually. After 10 minutes, different layers of chip were separated applying pressure at the joints and the middle layer was scanned with scanner after another 15 minutes.

Figure 8A:
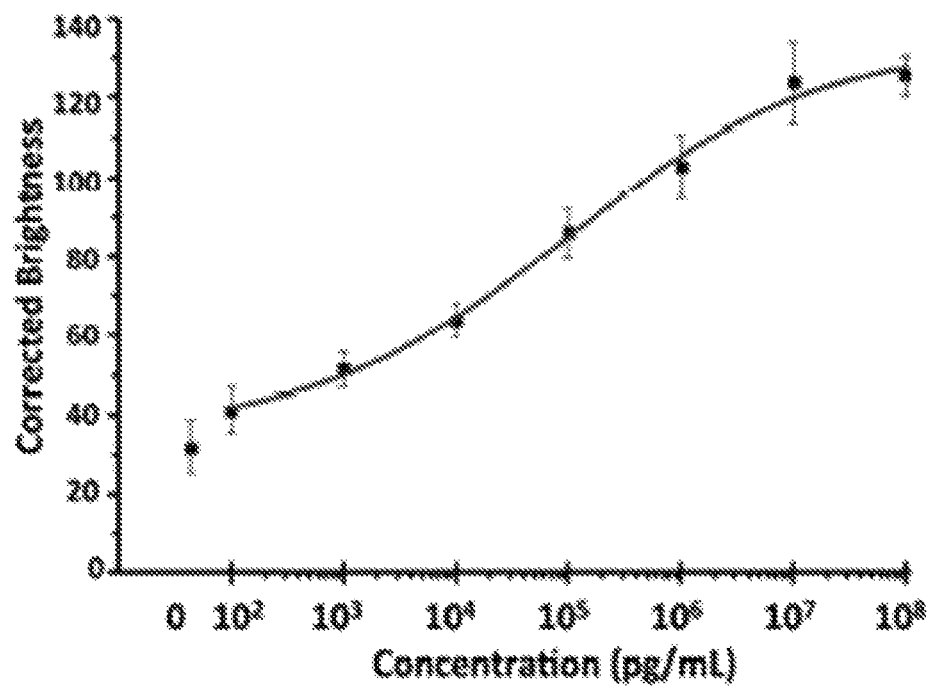
Figure 8B:
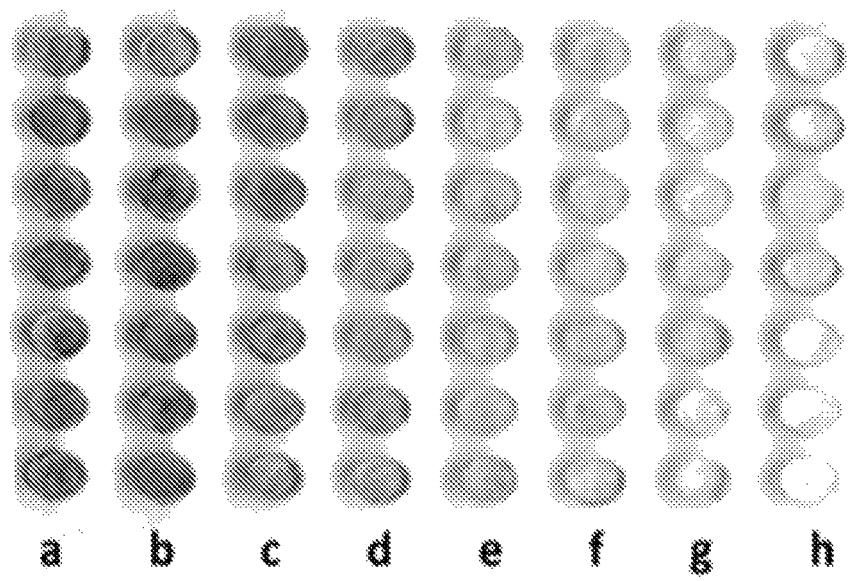

Signal intensities of the scanned images were quantified using ImageJ. FIG. 8 Calibration curve for the detection of IgG on a chip (A) Sigmoidal curve of IgG over a concentration range of $1\times10^2$ pg/mL to $1\times10^8$ pg/mL; (B) Enzymatic converted substrate in different columns of the chip with concentration; (a) 100 µg/mL, (b) 10 µg/mL, (c) 1 µg/mL, (d) 100 ng/mL, (e) 10 ng/mL, (f) 1 ng/mL, (g) 0.1 ng/mL, and (h) 0 ng/mL (PBS). FIG. 8A shows the calibration curve of IgG over a concentration range of $1\times10^2$ pg/mL to $1\times10^8$ pg/mL. A sigmoidal curve (FIG. 8A) was observed over the whole detected concentration range, while the linearity lies between $1\times10^3$ pg/mL to $1\times10^7$ pg/mL, which illustrates typical immunoassay characteristics. FIG. 8B, shows the increasing brightness value as the concentration goes on decreasing from 100 µg/mL to 0.1 ng/mL (left to right) and blank on the rightmost column, which can be seen through the naked eyes.

The limit of detection (LOD) is defined as the concentration value that generates a signal three standard deviation above the blank value. The calibration curve of IgG was linear over the range of $1\times10^3$ pg/mL to $1\times10^7$ pg/mL with the $R^2$ value of 0.993). The detection limit for IgG was found to be 1.6 ng/mL.

Example 2: HBsAg Detection Assay

Hepatitis B virus (HBV) infection is a major cause of chronic hepatic damage and of hepatocellular carcinomas worldwide. HBsAg, a qualitative serological biomarker for a developing HBV infection, can diagnose acute and chronic hepatitis B virus. Also, the titer of serum HBsAg indicates the level of infection and severity of disease.

Different concentration of HBsAg (0.34 ng/mL-340 µg/mL in 10 mM, pH 8.0 PBS) was introduced to the chip from different inlet holes in the first layer of the chip. After the chip was incubated with antigen for 10 minutes, the unreacted paper surface was blocked with Bovine Serum Albumin (4% BSA w/v in PBS+0.05% Tween 20) for another 10 minutes. After that, primary antibody i.e., anti-HBsAg was added and incubated for 10 minutes. It was washed once with washing buffer, PBST (10 mM, pH 7.4 PBS+0.05% Tween 20). Following washing, alkaline phosphatase labeled secondary antibody (29 µg/mL) was added. It was again incubated for another 7 minutes. Then, the final wash was done with washing buffer for three times. Finally, the substrate for the alkaline phosphatase, i.e., BCIP/NBT was added. After 10 minutes, different layers of chip were separated manually at the joints and the middle layer was scanned with scanner after another 15 minutes. Signal intensities of the scanned images were quantified using ImageJ.

FIG. 9 Calibration curve for the detection of HBsAg on a chip (A) Sigmoidal curve of HBsAg over a concentration range of $3.4\times10^2$ pg/mL to $3.4\times10^8$ pg/mL; (inset) Schematic for the colorimetric ELISA for detection of HBsAg, where a primary antibody (rabbit anti-HBsAg) and an ALP-conjugated secondary antibody (goat anti-rabbit IgG) are used together to label the HBsAg. ALP converts yellow substrate, BCIP/NBT into insoluble purple NBT Diformazan. (B) Enzymatic converted substrate in different columns of the chip with concentration; (a) 340 µg/mL, (b) 34 µg/mL, (c) 3.4 µg/mL, (d) 340 ng/mL, (e) 34 ng/mL, (f) 3.4 ng/mL, (g) 0.34 ng/mL, and (h) 0 ng/mL (PBS).

Figure 9A:
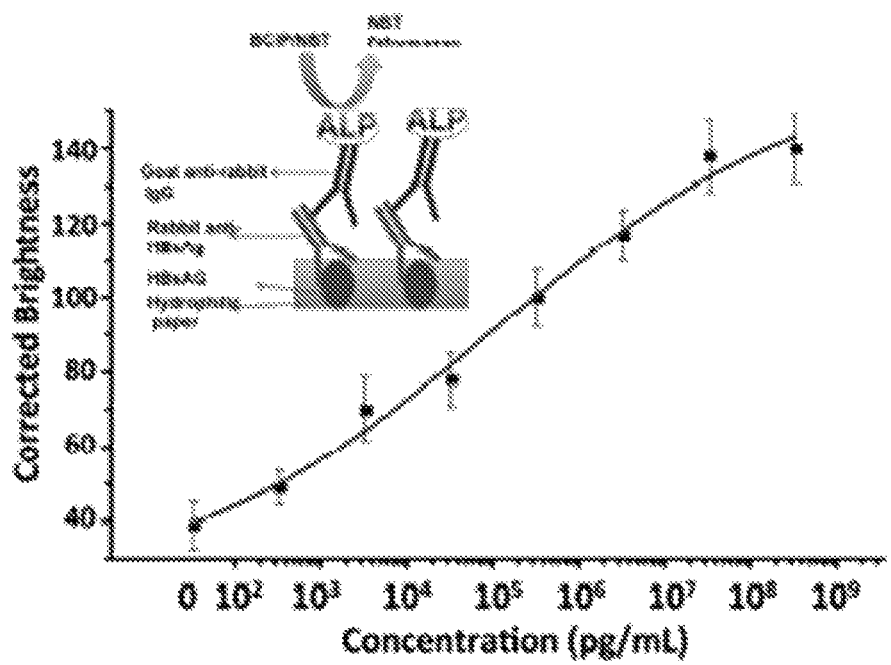
Figure 9B:
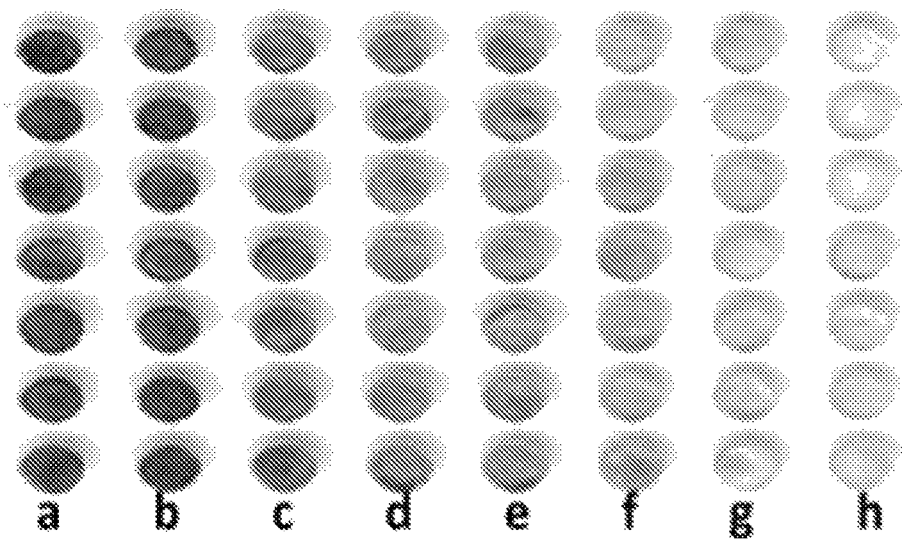

FIG. 9A shows the calibration curve of HBsAg over a concentration range of $3.4\times10^2$ pg/mL to $3.4\times10^8$ pg/mL. A sigmoidal curve was observed over the whole concentration range. The range of linearity was observed between $3.4\times10^2$ pg/mL to $3.4\times10^7$ pg/mL. FIG. 9B shows the increase in brightness value with decrease in concentration from 340

μg/mL to 0.34 ng/mL (left to right) with blank in the rightmost column. The limit of detection (LOD) is defined as the concentration value that generates a signal three standard deviation above the blank value. The calibration curve of HBsAg was linear over the range of $3.4 \times 10^2$ pg/mL to $3.4 \times 10^7$ pg/mL with the $R^2$ value of 0.990). The detection limit for HBsAg was found to be 1.3 ng/mL.

Example 3: Detection of HBcAg

For HBcAg detection assay, the Antigen, HBcAg (1 ng/mL-100 μg/mL in 10 mM, pH 8.0 PBS) was pipetted to the chip. After the chip was incubated with antigen for 10 minutes, the unreacted paper surface was blocked with Bovine Serum Albumin (4.5% BSA w/v in PBS+0.05% Tween 20) for another 10 minutes. After that, it was washed with washing buffer, PBST (10 mM, pH 7.4 PBS+0.05% Tween 20). Following washing, anti-HBcAg was added and incubated for 10 more minutes. It was washed once with washing buffer, PBST. Following washing, alkaline phosphatase labelled secondary antibody (6 μg/mL) was added. It was then incubated for another 7 minutes. Then, the final wash was done with washing buffer for three times. Finally, the substrate for the alkaline phosphatase, i.e., BCIP/NBT (Nitroblue tetrazolium+5-bromo, 4-chloro, 3-indoyl phosphate) was added. NBT is used with the alkaline phosphatase substrate BCIP in western blotting and immunohistological staining and immunoassay procedures. These substrate systems produce an insoluble NBT diformazan, end product that is blue to purple in color and can be observed visually. After 10 minutes, the chip was separated. Finally, the chip was scanned with scanner after 15 more minutes. The brightness value was measured by using the software ImageJ.

Figure 10A:
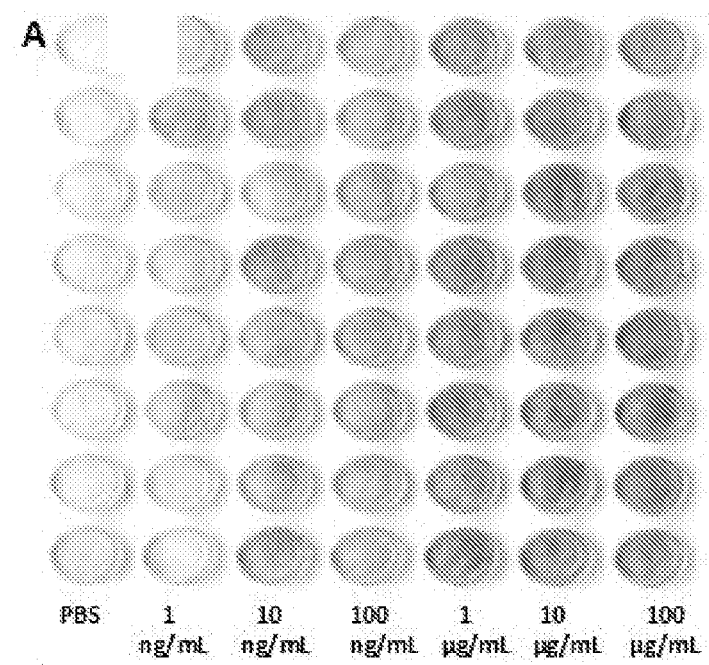
Figure 10B:
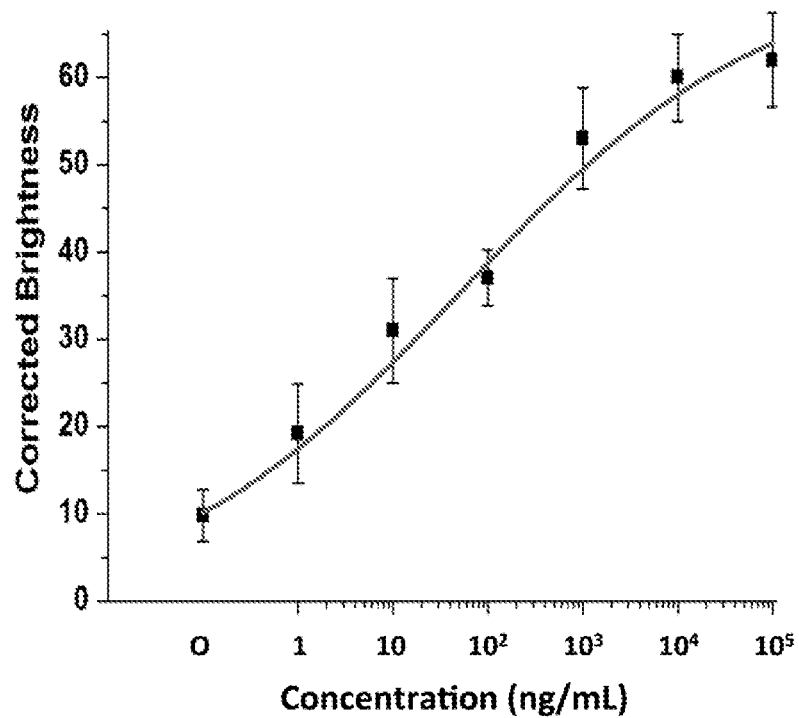

Similar to Example 1 disclosed herein, FIG. 10 illustrates the detection of HBcAg on a paper/PMMA hybrid microfluidic microplate. FIG. 10A is a scanned image of enzymatic converted substrate in different columns of the chip with concentrations from left to right: blank, 1 ng/mL, 10 ng/mL, 100 ng/mL, 1 μg/mL, 10 μg/mL, and 100 μg/mL respectively. FIG. 10B is a sigmoidal curve of the corrected brightness of HBcAg over a concentration range of 1 ng/mL to $10^5$ ng/mL. The calibration curve of HBcAg was linear over the range of 1 ng/mL to $1 \times 10^4$ ng/mL with a regression curve of y=10.36 log (x)+19.32 ($r^2$=0.98). The LOD of HBcAg was found to be 1.1 ng/mL in Example 3.

Example 4: Multiplexed Detection

The hybrid apparatus of Example 3 was used for simultaneous colorimetric detection of HBsAg and HBcAg. As shown in the diagram first column is negative control without any antigen, hence no color development. The second and third columns are for the detection of HBsAg while the fourth and fifth columns are for the detection of HBcAg. The third and fourth columns do not develop color, as they do not have the respective antibody against the antigen but the second and fifth columns develop color as they have their respective antibody. The sixth, seventh and eight columns have both the antigen i.e. HBsAg and HBcAg. All of them develop color as they have their respective antibody or the mixture of both the antibody.

Figure 11A:
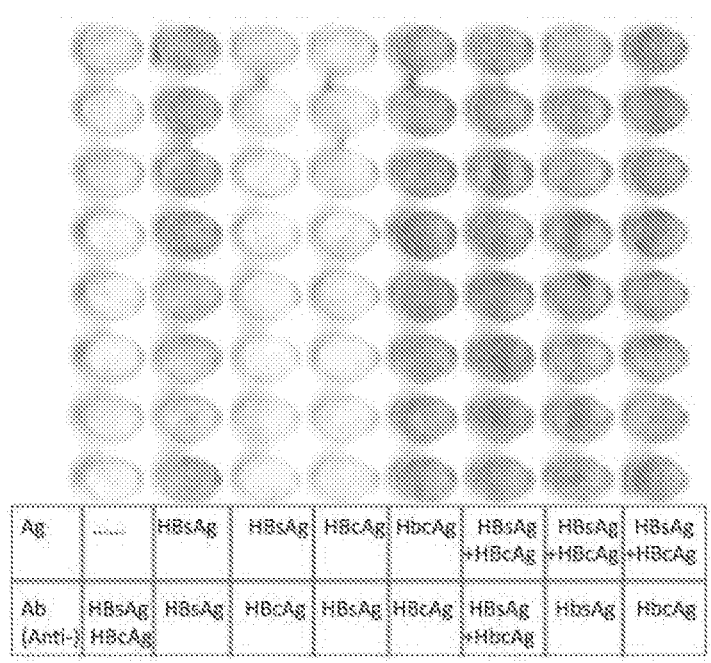
Figure 11B:
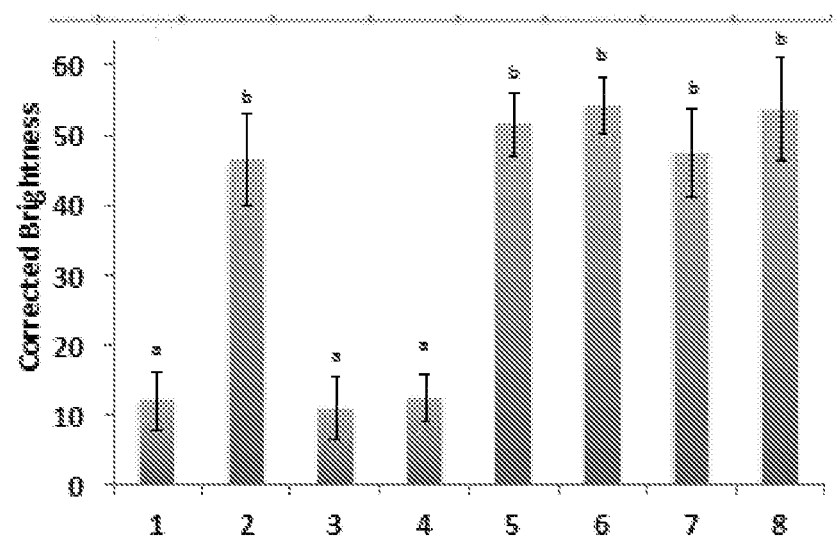

FIG. 11 illustrates a multiplex assay on a paper/PMMA hybrid microfluidic microplate. FIG. 11A depicts a scanned image of the enzyme-catalyzed substrate, while FIG. 11B is a bar plot of corrected brightness of the scanned image for detection of HBsAg and HBcAg. From left to right: immobilized probe, none (1), HBsAg (2) and (3), HBcAg (4) and (5), and HBsAg+HBcAg (6), (7), and (8), respectively. Test: From left to right, solution containing, anti-HBsAg and anti-HBcAg (1) and (6), HBsAg (2), (4), and (7), and HBcAg (3), (5), and (8). "a" and "b" shows that the data are significantly different from each other at p=0.05.

Example 5: Anti-Interference Test

The detection assay needs to have a high anti-interference capability to screen various infectious diseases as the serum contains complex ingredients consisting of hundreds of different proteins with a wide range of concentration that may interfere the detection of target proteins. So, FIG. 12 summarizes the results of anti-interference experiments in the various columns of the hybrid microfluidic microplate apparatus of the present disclosure. The experiment shows the detection of HBsAg 200 ng/mL with and without various interfering proteins (1 μg/ml, HBcAg, 100 ng/mL carcinoembryonic antigen (CEA), 250 μg/mL BSA, and 10 ng/mL prostate specific antigen (PSA)). As shown in the diagram, the first four columns do not contain HBsAg while the last four columns contains 200 ng/mL of HBsAg with various concentration of interfering proteins. In the absence of HBsAg, there is no development of color. Furthermore, the color intensity for the detection of 200 ng/mL of HBsAg in the presence of different interfering protein was similar to the detection of 200 ng/mL of HBsAg without the interfering protein. FIG. 12 demonstrates that even 1,250 times concentrated interfering proteins could not influence the specific detection of HBsAg.

Figure 12A:
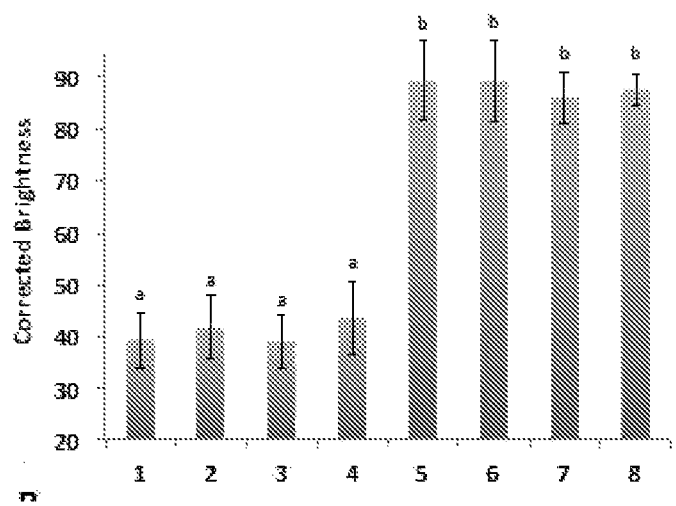
Figure 12B:
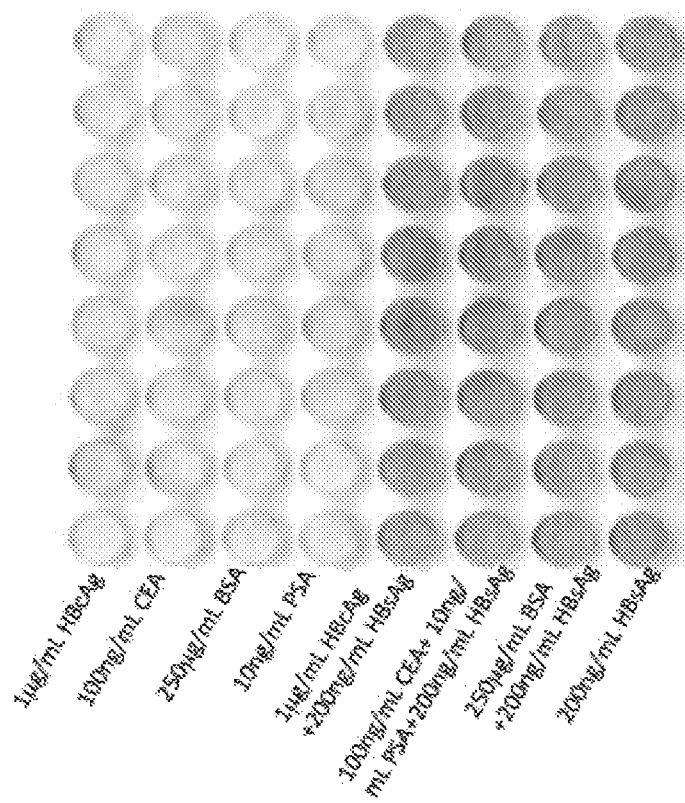

FIG. 12 depicts the results of an anti-interference test for the detection of HBsAg on a paper/PMMA hybrid microfluidic microplate. Corrected brightness of the scanned image of ELISA as measured by ImageJ (FIG. 12A) and scanned image of the chip (FIG. 12B) for the detection of HBsAg. From left to right: detection of 0 ng/mL of HBsAg in the solution containing 1 μg/mL HBcAg (1), 100 ng/mL CEA (2), 250 μg/mL BSA (3), and 10 ng/mL PSA (4), respectively and 200 ng/mL of HBsAg in 1 μg/mL HBcAg (5), 100 ng/mL CEA+10 ng/mL PSA (6), 250 μg/mL BSA (7), and PBS (8), respectively. "a" and "b" shows that the data are significantly different from each other at p=0.05.

The hybrid microfluidic microplate immunoassay apparatuses and methods disclosed herein possesses remarkable features such as high surface-to-volume ratio and microliter volume of microchannel that leads to significant decrease in analysis time from hours to minutes and with minimal reagent utilization as compared to regular ELISA technology. There is higher significance of this research for people in remote regions such as those found in underdeveloped and developing countries, in emergency situations, or in home health-care settings for early, easy and fast medical diagnosis. Hepatitis B virus (HBV) infection is a major cause of chronic hepatic damage and of hepatocellular carcinomas worldwide. HBsAg, a qualitative serological biomarker for a developing HBV infection, can diagnose acute and chronic hepatitis B virus. Also, the titer of serum HBsAg indicates the level of infection and severity of disease. IgG can serve as a specific marker for Neuromyelitis optica, an inflammatory demyelinating disease.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered.

This disclosure may include descriptions of various benefits and advantages that may be provided by various embodiments. One, some, all, or different benefits or advantages may be provided by different embodiments. In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A hybrid microfluidic microplate apparatus comprising:
a top layer comprising at least one inlet reservoir coupled to a microchannel,
a middle layer positioned beneath the top layer, said middle layer comprises at least one funnel shaped well comprising an upper well portion having a first diameter of 1 mm (millimeter) to 5 mm and a lower well portion having a second diameter of 0.1 mm to 1 mm, wherein a top portion of the upper well portion is connected to the microchannel in the top layer, and a bottom portion of the upper well portion is connected to a top portion of the lower well portion through a junction, and the second diameter is smaller than the first diameter,
an insert positioned inside the upper well portion and over the junction of the upper well portion and the lower well portion, said insert forms a separate layer within the at least one funnel shaped well and is made of a first material comprising a porous paper comprising cellulose, nitrocellulose, nylon, or any combinations thereof, and
a bottom layer positioned beneath the middle layer, said bottom layer comprises an outlet hole coupled to at least one outlet channel, said at least one outlet channel is coupled to a bottom portion of the lower well portion, and the outlet hole is fluidly connected to the inlet reservoir via the microchannel in the top layer, upper well portion, lower well portion, and at least one outlet channel,
wherein the top layer, the middle layer and the bottom layer is made with a second material comprising a polymer.

2. The apparatus of claim 1, wherein the polymer is selected from the group consisting of a poly(methyl methacrylate) (PMMA), a polydimethylsiloxane (PDMS), a polycarbonate (PC), and a polyethylene terephthalate (PETG).

* * * * *